(12) United States Patent
Markman

(10) Patent No.: US 11,877,921 B2
(45) Date of Patent: Jan. 23, 2024

(54) METHOD AND APPARATUS FOR CREATING A MODIFIED TISSUE GRAFT

(71) Applicant: Markman Biologics Corporation, Las Vegas, NV (US)

(72) Inventor: Barry Markman, Frisco, TX (US)

(73) Assignee: MARKMAN BIOLOGICS CORPORATION, Las Vegas, NV (US)

( * ) Notice: Subject to any disclaimer, the term of this patent is extended or adjusted under 35 U.S.C. 154(b) by 509 days.

(21) Appl. No.: 16/831,169

(22) Filed: Mar. 26, 2020

(65) Prior Publication Data

US 2020/0222167 A1    Jul. 16, 2020

Related U.S. Application Data

(63) Continuation-in-part of application No. 16/657,124, filed on Oct. 18, 2019, now Pat. No. 11,701,213, (Continued)

(51) Int. Cl.
*A61F 2/02* (2006.01)
*A61F 2/00* (2006.01)
*A61L 27/54* (2006.01)

(52) U.S. Cl.
CPC .......... *A61F 2/0077* (2013.01); *A61F 2/0063* (2013.01); *A61L 27/54* (2013.01);
(Continued)

(58) Field of Classification Search
CPC ........ A61F 2/00; A61F 2/0077; A61F 2/0063; A61F 2/02; A61F 2/0059; A61F 2/12; A61F 2002/0068; A61F 2002/0081; A61L 27/54
See application file for complete search history.

(56) References Cited

U.S. PATENT DOCUMENTS

| 4,950,296 A | 8/1990 | McIntyre |
| 5,728,159 A | 3/1998 | Stroever et al. |

(Continued)

FOREIGN PATENT DOCUMENTS

| CN | 105165803 | 12/2015 |
| WO | 2001045566 | 6/2001 |

OTHER PUBLICATIONS

PCT Search Report and Written Opinion for International Application No. PCT/US2021/022691, dated Aug. 31, 2021, 15 pages.
(Continued)

*Primary Examiner* — Vi X Nguyen
(74) *Attorney, Agent, or Firm* — Weide & Miller, Ltd.

(57) ABSTRACT

In a method of creating a modified tissue graft, at least one exterior surface of a graft is modified by compressing, cutting and/or removing one or more portions thereof, such as to create designed surface features which cause the tissue graft to have characteristics for a specific anatomical area. The modified tissue graft may include a medicated graft, such as by associating medicants with the surface features, or by associating a second graft or layer with a modified base tissue graft layer, where medicants are associated with the second graft or layer. The tissue graft may be modified by pressing a specially configured template or die, such as having blades thereon, into the tissue graft, such as to create a pattern of partial depth cuts.

7 Claims, 13 Drawing Sheets

Related U.S. Application Data which is a continuation-in-part of application No. 16/410,167, filed on May 13, 2019, now Pat. No. 11,246,697, which is a continuation of application No. 15/487,585, filed on Apr. 14, 2017, now Pat. No. 10,285,795, which is a continuation of application No. 14/678,188, filed on Apr. 3, 2015, now Pat. No. 9,622,845, which is a continuation-in-part of application No. 13/687,082, filed on Nov. 28, 2012, now Pat. No. 9,050,177, which is a continuation of application No. 13/101,022, filed on May 4, 2011, now Pat. No. 8,858,647.

(60) Provisional application No. 62/805,032, filed on Feb. 13, 2019, provisional application No. 61/331,805, filed on May 5, 2010.

(52) U.S. Cl.
CPC ............... *A61F 2002/0068* (2013.01); *A61F 2002/0081* (2013.01); *A61F 2240/002* (2013.01); *A61F 2240/005* (2013.01); *A61F 2250/0026* (2013.01); *A61F 2250/0048* (2013.01); *A61F 2250/0051* (2013.01); *A61F 2250/0067* (2013.01)

(56) References Cited

U.S. PATENT DOCUMENTS

| | | | |
|---|---|---|---|
| 5,759,205 A | 6/1998 | Valentini | |
| 5,935,002 A | 8/1999 | Falciglia | |
| 5,971,849 A | 10/1999 | Falciglia | |
| 6,190,255 B1 | 2/2001 | Thomas et al. | |
| 6,280,328 B1 | 8/2001 | Holch et al. | |
| 6,911,220 B1 | 6/2005 | Sachs | |
| 6,949,252 B2 | 9/2005 | Mizuno et al. | |
| 7,066,962 B2 | 6/2006 | Swords | |
| 7,189,259 B2 | 3/2007 | Simionescu et al. | |
| 7,282,165 B2 | 10/2007 | Williams, III et al. | |
| 7,416,546 B2 | 8/2008 | Pugsley et al. | |
| 7,427,284 B2 | 9/2008 | Seedhom et al. | |
| 7,458,975 B2 | 12/2008 | May et al. | |
| 7,520,898 B2 | 4/2009 | Re et al. | |
| 7,572,298 B2 | 8/2009 | Roller et al. | |
| 7,645,568 B2 | 1/2010 | Stone | |
| 7,723,108 B2 | 5/2010 | Truncale et al. | |
| 7,727,278 B2 | 6/2010 | Olsen et al. | |
| 7,776,089 B2 | 8/2010 | Bianchi et al. | |
| 7,815,923 B2 | 10/2010 | Johnson et al. | |
| 8,372,437 B2 | 2/2013 | Daniel | |
| 8,460,715 B2 | 6/2013 | Daniel | |
| 8,500,740 B2 | 8/2013 | Bojarski et al. | |
| 8,597,687 B2 | 12/2013 | Daniel | |
| 8,741,646 B2 | 6/2014 | Emig et al. | |
| 8,858,647 B2 | 10/2014 | Markman | |
| 9,050,177 B2 | 6/2015 | Markman | |
| 9,622,845 B2 | 4/2017 | Markman | |
| 10,105,862 B1 | 10/2018 | Koch et al. | |
| 11,246,697 B2 * | 2/2022 | Markman | ........... A61L 27/3683 |
| 11,701,213 B2 | 7/2023 | Markman | |
| 2003/0036770 A1 * | 2/2003 | Markman | .......... A61B 17/3468 606/187 |
| 2004/0049270 A1 | 3/2004 | Gewirtz | |
| 2004/0057938 A1 | 3/2004 | Ghinelli | |
| 2004/0082063 A1 | 4/2004 | Deshpande et al. | |
| 2006/0018838 A1 | 1/2006 | George et al. | |
| 2006/0219143 A1 | 10/2006 | Brennan et al. | |
| 2007/0061015 A1 | 3/2007 | Jensen et al. | |
| 2009/0291116 A1 | 11/2009 | Casellas | |
| 2010/0119755 A1 | 5/2010 | Chung et al. | |
| 2010/0137903 A1 | 6/2010 | Lee et al. | |
| 2010/0161032 A1 | 6/2010 | Avellanet | |
| 2010/0228335 A1 | 9/2010 | Schorgl et al. | |
| 2011/0022171 A1 | 1/2011 | Richter et al. | |
| 2014/0348940 A1 | 11/2014 | Murphy et al. | |
| 2015/0139960 A1 | 5/2015 | Tumey et al. | |
| 2015/0209128 A1 | 7/2015 | Markman | |
| 2015/0342725 A1 | 12/2015 | Cuevas et al. | |
| 2016/0256259 A1 | 9/2016 | Wirth et al. | |
| 2017/0367807 A1 | 12/2017 | Chen et al. | |
| 2018/0228938 A1 | 8/2018 | McGuire et al. | |

OTHER PUBLICATIONS

USPTO, Notice of Allowance dated Mar. 15, 2023, U.S. Appl. No. 16/657,124, 12 pages.
International Search Report and Written Opinion dated Jan. 6, 2020, in PCT/US2019/057005, 8 pgs.

* cited by examiner

| EXAMPLE | | GRAFT |
|---|---|---|
| A | ANATOMIC AREA: KNEE / SHOULDER<br>FUNCTION: STABILIZE MOTION<br>DIE: INVERVAL<br>RESURFACE: LATERAL - HEAVY  MIDDLE - NONE<br>GOAL: ADHESION AT OSSEOUEORIGIN INSERTION / GLIDE MIDDLE | |
| B | ANATOMIC AREA: KNEE/HIP/ANKLE<br>FUNCTION: STABILIZE FRACTURES<br>DIE: INTERVAL<br>RESURFACE: DERMAL - HEAVY<br>GOAL: OSSEOUS HEALING | |
| C | ANATOMIC AREA: BREAST /ABDOMEN<br>FUNCTION: REINFORCEMENT SOFT TISSUE/PRESSURE RELEASE<br>DIE: INTERVAL/ LINEAR<br>RESURFACE: DERMAL LATERAL - HEAVY  MIDDLE - MEDIUM   SUPERIOR - INFERIOR SURFACE<br>GOAL: LATERAL - REINFORCEMENT  MIDDLE - ADHESION  SUPERIOR SUPERIOR PRESSURE RELEASE | SUPERIOR ADIPOSE / INFERIOR - MUSLCE |
| D | ANATOMIC AREA: SKIN<br>FUNCTION: CLOSURE UNDER TENSION  RE RESECTION<br>DIE: INTERVAL/LINEAR<br>RESURFACE: DHAC  LATERAL- MEDIUM   MIDDLE - HEAVY<br>GOAL: SCAR REDUCTION | |
| E | ANATOMIC AREA: DENTAL<br>FUNCTION: MASTICATION<br>DIE: INTERVAL<br>RESURFACE: DERMAL<br>GOAL: OSSEOUS INTEGRATION | |
| F | ANATOMIC AREA: CANCER RESECTION<br>FUNCTION: N/A<br>DIE: INTERVAL/LINEAR<br>RESURFACE: dHAC overlay/Dermal combination<br>GOAL: DECREASE CANCER RECURRANCE | |
| G | ANATOMIC AREA: INFECTION : SKIN/DENTAL /INTERNAL<br>FUNCTION: N/A<br>DIE: INTERVAL/LINEAR<br>RESURFACE: dHAC overlay w or wo Dermal combination<br>GOAL: INCREASE RATE OF HEALING AFTER INFECTION | |

FIG. 5

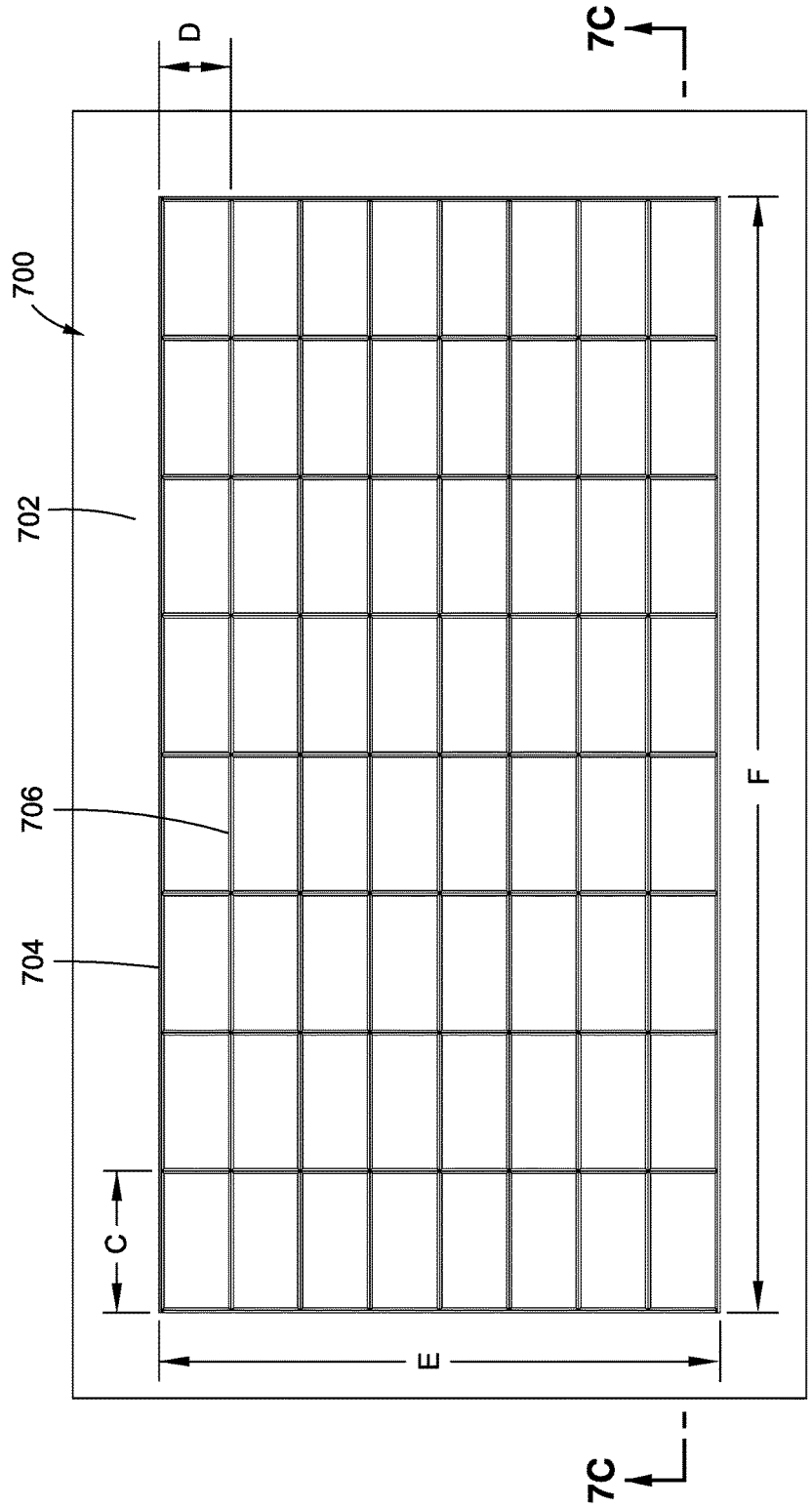
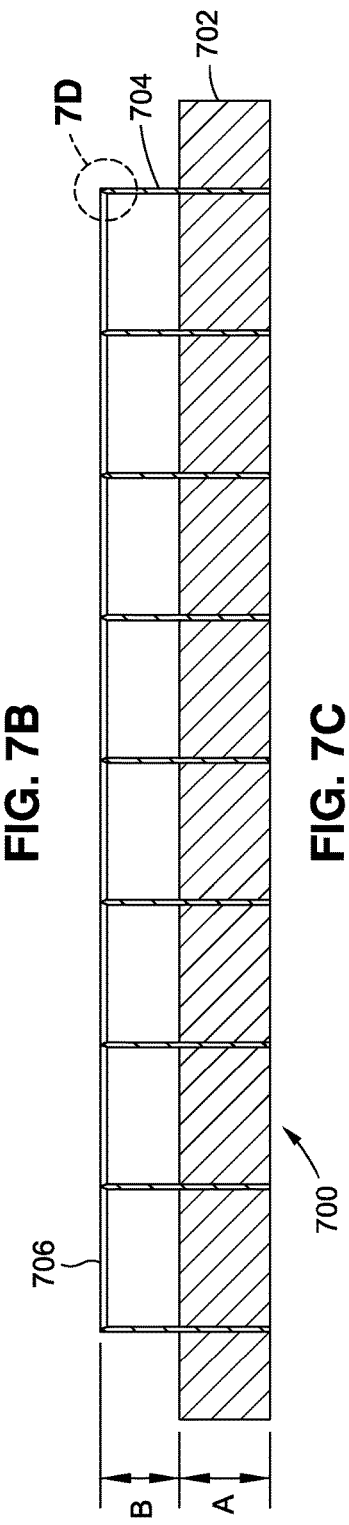
FIG. 7B
FIG. 7C

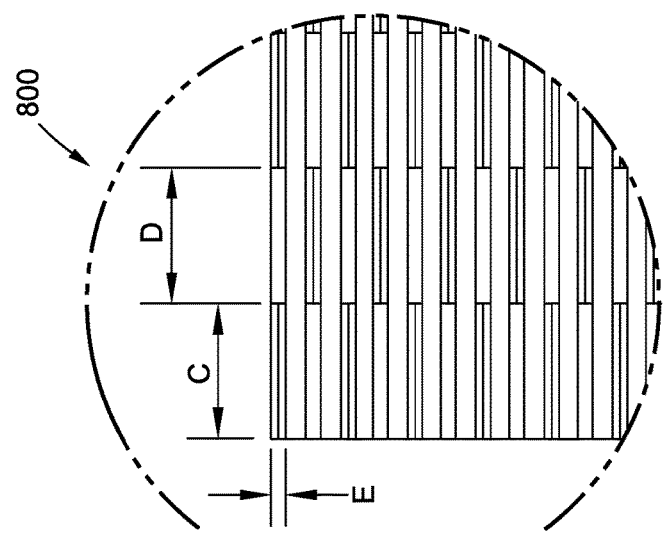
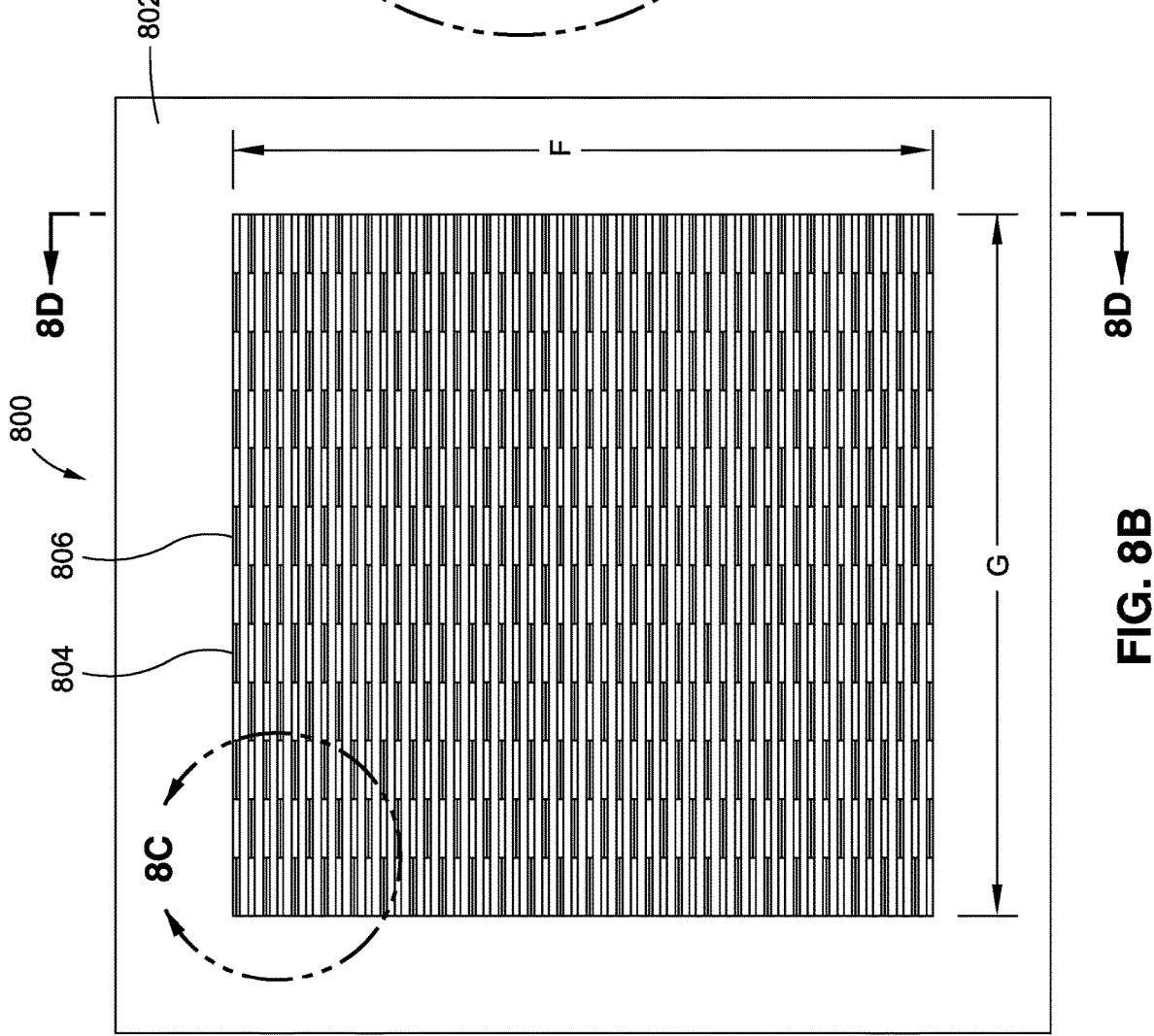
FIG. 8C
FIG. 8B

METHOD AND APPARATUS FOR CREATING A MODIFIED TISSUE GRAFT

RELATED APPLICATION DATA

This application is a continuation-in-part of U.S. application Ser. No. 16/657,124, filed Oct. 18, 2019, which claims priority to U.S. Provisional Application Ser. No. 62/805,032, filed Feb. 13, 2019, and which is a continuation-in-part of U.S. application Ser. No. 16/410,167, filed May 13, 2019, which is a continuation of U.S. application Ser. No. 15/487,585, filed Apr. 14, 2017, now U.S. Pat. No. 10,285,795, issued May 14, 2019, which is a continuation of U.S. application Ser. No. 14/678,188, filed Apr. 3, 2015, now U.S. Pat. No. 9,622,845, issued Apr. 18, 2017, which is a continuation-in-part of U.S. application Ser. No. 13/687,082, filed Nov. 28, 2012, now U.S. Pat. No. 9,050,177, issued Jun. 9, 2015, which is a continuation of U.S. patent application Ser. No. 13/101,022, filed May 4, 2011, now U.S. Pat. No. 8,858,647, issued Oct. 14, 2014, and claims priority to U.S. Provisional Application Ser. No. 61/331,805, filed May 5, 2010; the contents of said earlier applications are incorporated by reference in their entirety herein.

FIELD OF THE INVENTION

The present invention relates to tissue grafts with resurfacing in a targeted methodology based on anatomic location and medical functional indications.

BACKGROUND OF THE INVENTION

Current surgical reconstruction of tissue defects utilizes a solid, porous sheet with or without perforations. Current grafts allow for perforations that do enhance fluid egress and in growth of new tissue, but due to the constrictive nature of such tissue grafts, the incidences of recurrences and the inability to expand with the application of increased pressure has allowed for a significant incidence of recurrence, stress tears, and an inability for expansion used in reconstructive and aesthetic procedures. Current tissue grafts also do not allow for the ability to enhance the graft as it is placed between specific anatomic points.

BRIEF DESCRIPTION OF THE FIGURES

FIG. 5 is a table which illustrates aspects of targeted resurfacing in accordance with an embodiment of the invention;

FIGS. 7A-7D illustrate one embodiment of a tissue graft cutting die in accordance with an embodiment of the invention;

FIGS. 8A-8E illustrate another embodiment of a tissue graft cutting die in accordance with an embodiment of the invention;

SUMMARY OF THE INVENTION

Figure 1:
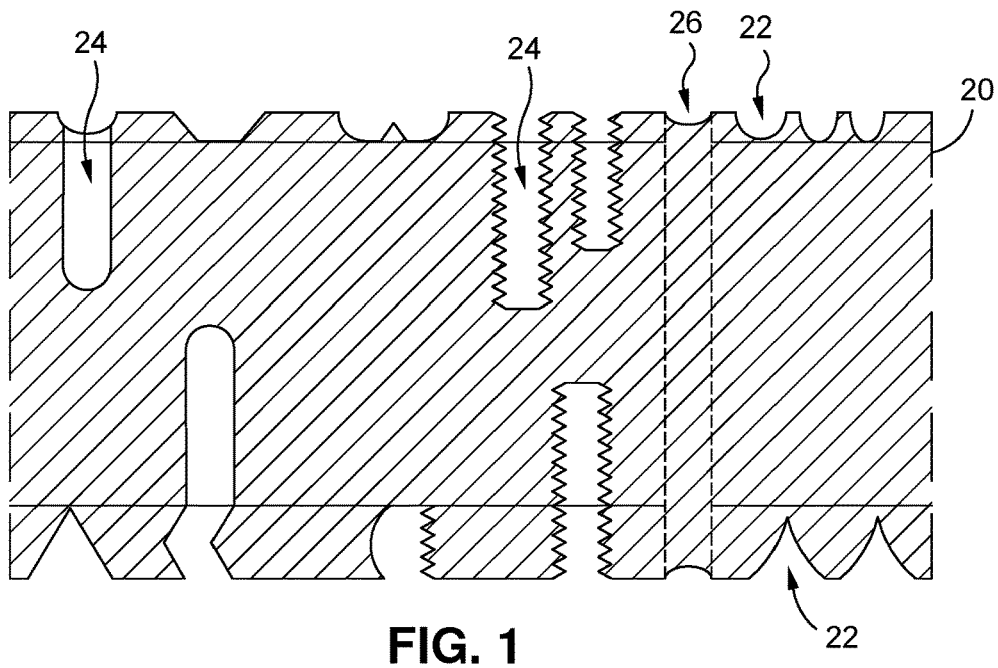
FIG. 1 is a side view of a tissue graft having various surface patterns in accordance with an embodiment of the invention, which patterns may be used to contain or retain medicants, tissues or other materials in accordance with other embodiments of the invention.

Various methods and apparatus for creating a modified tissue graft, and most preferably, an external tissue graft, are disclosed.

Aspects of the invention comprise modified tissue grafts and methods of creating a modified tissue graft by modifying a tissue graft, such as by cutting, compressing and/or removing areas of the initial tissue graft, such as at a top or bottom surface thereof.

In one embodiment, the invention is configured to, and an advantage of the invention comprises, allowing for faster wound healing by promoting vascular ingrowth of the body's tissue in specific areas due to targeted resurfacing of the modified tissue graft.

In one embodiment, the invention is configured to, and an advantage of the invention comprises, allowing for reduced scaring by decreasing ingrowth of the body's tissue in specific areas due to targeted resurfacing of the modified tissue graft.

In one embodiment, the invention is configured to, and an advantage of the invention comprises, reducing stress in grafts subject to continuous motion, such as, in the knee, hip, and cervical region due to targeted resurfacing.

In one embodiment, the invention is configured to, and an advantage of the invention comprises, reducing stress in grafts subject to increased pressure gradients such as in the abdominal wall, inguinal hernia, and arterial grafts.

In one embodiment, the invention is configured to, and an advantage of the invention comprises, allowing for selective expandability (such as via partial or non-through expansion incisions and/or through expansion incisions of various thicknesses in the graft) in order to achieve better contour and external appearance due to targeted resurfacing.

In one embodiment, the invention is configured to, and an advantage of the invention comprises, allowing for selective expandability (such as via partial or non-through expansion incisions and/or through expansion incisions of various thicknesses in the graft) in order to achieve better outflow of blood in venous grafts due to targeted resurfacing.

In one embodiment, the invention is configured to, and an advantage of the invention comprises, allowing for selective traction or adhesion points of tissue grafts to key anatomic areas when needed in order to increase fixation at insertions and origins to reduce slippage due to targeted resurfacing of the graft.

In one embodiment, the invention is configured to, and an advantage of the invention comprises, allowing for an increase in the period of time of utilization and longevity of the modified tissue graft.

Another embodiment of the invention comprises methods and apparatus for creating a medicated graft, such as a tissue graft which includes a medicant, such as antibiotics, growth factors, or chemotherapeutics, or other tissues (such as stem cells), due to targeted resurfacing.

In one embodiment, one or more templates or dies are used to modify the surface of a tissue graft, such as to remove material from the graft, compress areas of the graft, cut areas of the graft, or otherwise alter at least a surface of the graft. Such modifications, such as cuts, may be full or partial thickness modifications. Such a template or die may comprise one or more blades and one or more stop surfaces, such as for limiting the depth of cut of the blades. The blades may be straight or curved/curvilinear (such as semi-circular) or combinations thereof. The blades might be arranged in rows, grids or the like, depending upon the desired modification (such as to create various patterns, etc.). The template may be pressed into the surface of the graft to modify it, such as via use of a pneumatic press.

In one embodiment, modifications are made to an initial tissue graft to create a modified tissue graft having certain characteristics or properties. The particular modifications and the areas where the modifications are made may be selected to achieve particular characteristics or properties in different areas of the modified tissue graft, such as based upon the desired use, including the particular anatomical location at which the modified tissue graft is to be used, as well as the functional and medical purpose the modified tissue graft is to serve.

Another embodiment of the invention comprises a multi-layer, medicated, reconstructive tissue graft. Such a graft may comprise a base tissue graft having a top surface and a bottom surface, the base tissue graft modified by compressing, cutting and/or removing one or more portions of either or both the top surface and the bottom surface to create one or more designed surface features, a second graft layer or sheet applied to either or both the top surface and the bottom surface of the base tissue graft, and one or more medicants associated with the multi-layer reconstructive graft.

Relative to such a multi-layer graft, the medicants may be associated with the designed surface features of the base graft and then the second graft layer is placed over the designed surface features. In another embodiment, the medicants are associated with the second graft layer or sheet itself. In yet another embodiment, the medicants are injected or inserted into the base tissue graft through the second graft layer or sheet, such as using a needle.

Further objects, features, and advantages of the present invention over the prior art will become apparent from the detailed description of the drawings which follows, when considered with the attached figures.

DETAILED DESCRIPTION OF THE INVENTION

Aspects of the invention comprise methods of modifying a tissue graft to create a modified tissue graft, which tissue graft may have features which are selected to address particular objectives relative to a particular anatomical site; modified grafts, including modified tissue grafts which have features which are designed for particular medical indications and/or for a particular anatomical site; and methods of making one or more templates which are usable to modify a tissue graft to create a modified tissue graft, such as by cutting or removing portions of the tissue graft or otherwise create surface patterns or other features.

One embodiment of the invention is a tissue graft having features which are selected or designed to address particular objectives, such as relative to a particular anatomical site, medical condition or the like. In a preferred embodiment, the tissue grafts are modified tissue grafts—e.g. an initial tissue graft which does not have all of the desired features or characteristics which is then modified or altered to create a modified tissue graft which has desired features or characteristics.

In one embodiment of the invention, the tissue grafts comprise cadaveric human tissue, or may comprise amniotic or chorionic tissue (including genetically altered human de-cellular amniotic and/or chorionic tissue), or other tissue. In other embodiments, the tissue grafts may comprise cellular non-human tissue, including cellular and acellular processed grafts. The tissue grafts may also comprise synthetic materials. As indicated, in one embodiment, such a tissue graft is modified in accordance with the invention to create a modified graft.

As detailed herein, in various embodiments of the invention, tissue grafts are modified by cutting the graft, removing material from the graft, compressing one or more areas of the graft or otherwise altering the surface(s) of the graft to create a modified tissue graft. Such modifications may, as detailed below, be accomplished in various manners, including via the use of templates such as dies, cutting devices including interval cutting devices, or the like, which may be used to create such modifications.

FIG. 1 illustrates a tissue graft 20 in accordance with an embodiment of the invention. In accordance with the invention, the tissue graft 20 comprises a modified tissue graft where cutting, compression and/or removal of segments of graft material (such as spaced or separated by various distances between them) creates recessed expansion patterns (including slots, slits, depressions or openings) of various depths and shapes 22, adhesion projections of various heights and shapes 24, and through holes or openings 26 (including where the shape, location and/or orientation of the feature(s) is selected to achieve certain characteristics, such as expansion in certain directions, stress reduction in certain directions, etc.). The modifications may be partial depth or thickness and full or "through" depth or thickness. For example, cuts may be partial depth or thickness (e.g. extending into the surface of the graft some distance but not all of the way through the graft from top to bottom) or may be full depth or thickness (e.g. all of the way through the graft from top to bottom). Likewise, other modifications such as holes or openings might be partial or full depth. In some instances, combinations of partial and full depth modifications may be made.

Figure 2A:
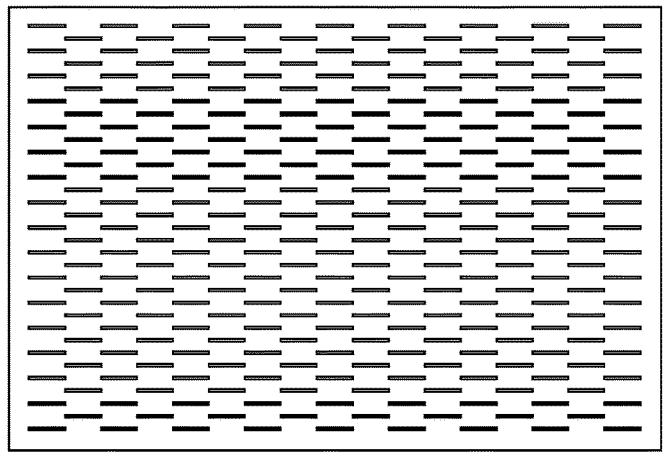
FIGS. 2A and 2B illustrate configurations of die cuts made to alter a tissue graft in accordance with embodiments of the invention.
Figure 2B:
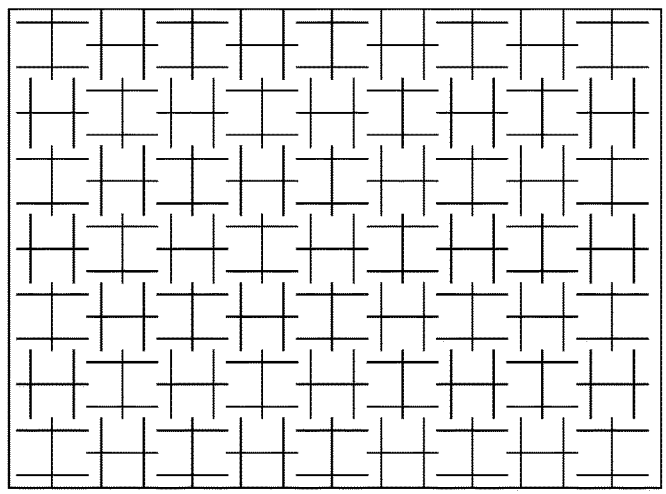

FIGS. 2A and 2B illustrate additional examples of tissue grafts 20 which have been modified in particular exemplary manners. In FIG. 2A, the tissue graft 20 has been modified to include a plurality of cuts or slits 30 at one or more portions of a surface thereof, such as a top surface. In the configuration which is illustrated, the cuts 30 are rows of offset cut segments which are aligned with one another. Such a configuration may be referred to as "linear" modification. This configuration might be achieved, for example, using a die having a plurality of blades which, when pressed into a tissue graft, form a modified tissue graft having the cuts or slits 30 as illustrated (wherein, as described below, the die may have blades with adjacent lateral flat struts or base surfaces which control the depth of cut).

Figure 3A:
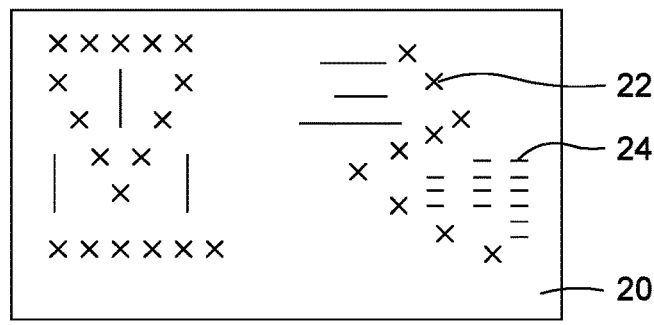
FIGS. 3A and 3B illustrate a top and bottom, respectively, of a tissue graft having patterns in accordance with the invention.
Figure 3B:
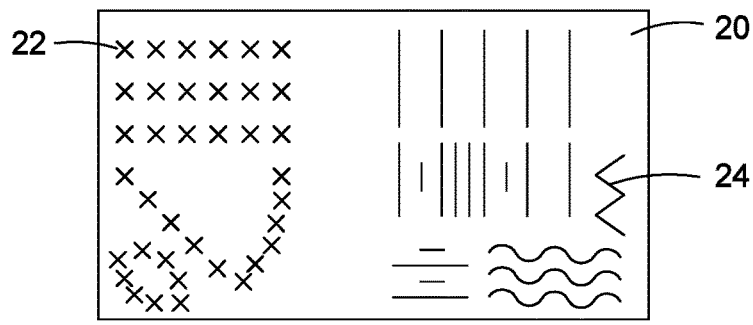

In other embodiments, a tissue graft may be modified to include one or more curved or curvilinear cuts or modifications. FIG. 3B illustrates, in the right-hand corner thereof, modification of a tissue graft to include non-linear cuts or modifications. Such a configuration may be achieved, for example, by use of a die having a plurality of curvilinear blades which, when passed into a tissue graft, form a modified tissue graft having curvilinear cuts or slits 30 (wherein, as describe below, the die may have blades with adjacent lateral flat struts or base surfaces which control the depth of cut). Of course, the blades might have various curved shapes, including semi-circular and irregular curved shapes, as well as in forms having combinations of linear and curved portions.

In FIG. 2B, a tissue graft 20 has been modified to include a pattern or cuts or slits 30 in one or more portions of a surface thereof, such as a top surface. In the configuration which is illustrated, various of the cuts 30 extend generally perpendicular to one another, and some of the cuts intersect, while others do not. Such a configuration may be referred to as "interval" modification. This configuration might be achieved, for example, using a die having a plurality of blades which, when pressed into a tissue graft, form a modified tissue graft having the cuts or slits 30 as illustrated.

As is described in more detail below, these modifications may have various configurations and locations, including being located across the entire surface of the graft, or only in one or more areas, or differing from area to area, and being on one side or both, such as depending upon the desired characteristics of the graft. It has been found, for example, that the "linear" modification illustrated in FIG. 2A results in the graft (or area thereof) having the characteristics of being expandable (particularly in a direction transverse to the direction of the cuts). On the other hand, the "interval" modification illustrated in FIG. 2B results in graft (or area thereof) having adhesion characteristics.

It will also be appreciated that the amount of modification to the graft, or an area thereof, may be used to control the characteristics of the modified graft. For example, relative to the example in FIG. 2B, a greater number of cuts 30 may be used when a high adhesion characteristic is desired, while a pattern of fewer cuts 30 might be used when a lower adhesion characteristic is desired.

As noted, different types of modifications might be made, including to different areas of a graft, to achieve modified tissue grafts with different characteristics. FIGS. 3A and 3B illustrate one example of patterns of adhesion features 22 and expansion features 24 relative to a top (in FIG. 3A) and bottom (in FIG. 3B) of a tissue graft 20, which patterns may be used to generate a tissue graft having particular desired characteristics for a particular application, such as described in more detail below relative to FIGS. 4 and 5 below.

The features of the tissue grafts may vary both in the nature of the modifications and the characteristics of the graft achieved thereby, not limited to the following: (1) the modifications (such as created patterns or features, such as cuts, voids, etc.) may vary by the distance between them and the modifications can be of various shapes, widths, thicknesses, and variegations; (2) the designated modifications or other features can be either full thickness or partial thickness of the graft; (3) the designated modifications can be on both anterior and posterior surfaces of the graft; (4) the designated modifications may be configured to provide enhanced controlled expansion of the tissue graft; (5) the designated modifications may be configured to provide enhanced stress relief during motion of the tissue graft; (6) the designated modifications may be configured to provide enhanced adhesion between the tissue graft and anatomic region; (7) the designated modifications may be configured to provide enhanced retention of various medicants and materials both in vitro and in vivo; and/or (8) the designated modifications may be configured to provide enhanced longevity and utilization of the graft.

Figure 3C:
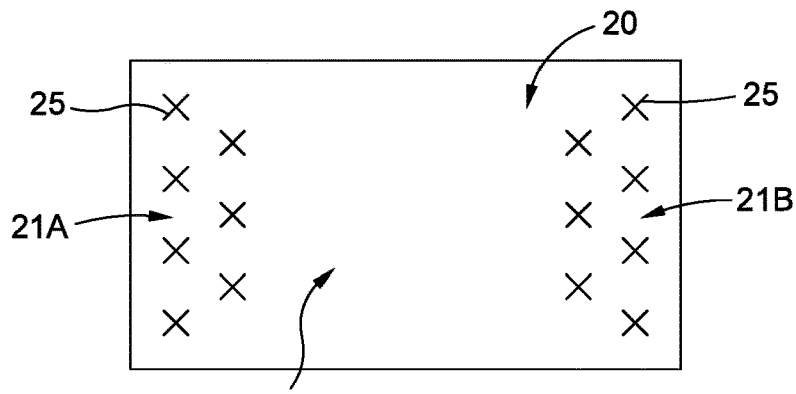
FIGS. 3C, 3D, 3E and 3F illustrate tissue grafts modified to have different areas with different surface patterns in accordance with embodiments of the invention.

As described in more detail below, aspects of the present invention comprise modified tissue grafts and methods of making the same so that the modified tissue graft has particular characteristics for addressing particular anatomical regions/issues and medical conditions. Such characteristics may comprise one or more of enhanced expansion, flexibility and/or stretch (such as when the tissue graft is to be wrapped about or around an anatomical area or part), traction, glide, adhesion, to reduce stress (such as shear forces), interaction of critical cells (between the graft and site tissue, such as increasing the depth and speed of penetration of the site tissue into the graft) or period of utilization in anatomic areas where it is placed. For example, in one embodiment, modified tissue grafts are configured to facilitate for faster wound healing by promoting vascular ingrowth of the body's tissue in specific areas due to targeted resurfacing of the modified tissue graft. As another example, in one embodiment, modified tissue grafts are configured to facilitate reduced scaring by decreasing ingrowth of the body's tissue in specific areas due to targeted resurfacing of the modified tissue graft. As illustrated in FIGS. 3A and 3B, different areas of a tissue graft may be modified in different manners to create a modified tissue graft having areas with different features or characteristics (which may be referred to as "targeted resurfacing"). For example, as illustrated in FIG. 3C, one or more templates might be utilized to modify the end regions 21A,B of a tissue graft 20 (but not a middle section 21C thereof) to create a modified tissue graft having features 25 with characteristics that increase traction at the ends 21A,B (such as by having surface features which are rough and promote adhesion) and which promotes glide in the middle 21C (such as by having a surface in the middle which is generally smooth). Such a modified tissue graft might, for example, have advantages when placed at a particular anatomic region such as a knee joint.

Figure 3D:
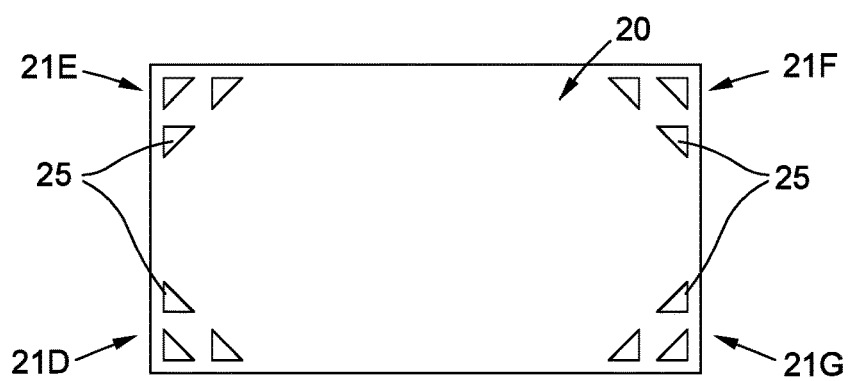

As another example and illustrated in FIG. 3D, one or more templates might be utilized to modify the corner regions 21D-G (but not the middle of) a tissue graft 20. The resultant modified tissue graft may thus include tissue modification features 25 at the corners 21D-G that have characteristics that are configured to reduce mechanical sheer forces which are applied to the modified graft, such as to reduce scar tissue formation.

Figure 3E:
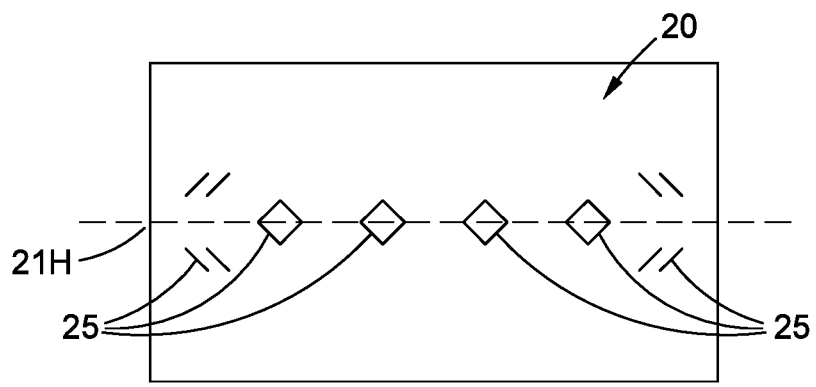

As yet another example as illustrated in FIG. 3E, one or more templates might be utilized to modify a midline portion 21H of a tissue graft 20. The resultant modified tissue graft might then have tissue modification features 25 along that centerline that have characteristics which facilitate wrapping of the modified tissue graft around an object, such as an anastomosis.

Figure 3F:
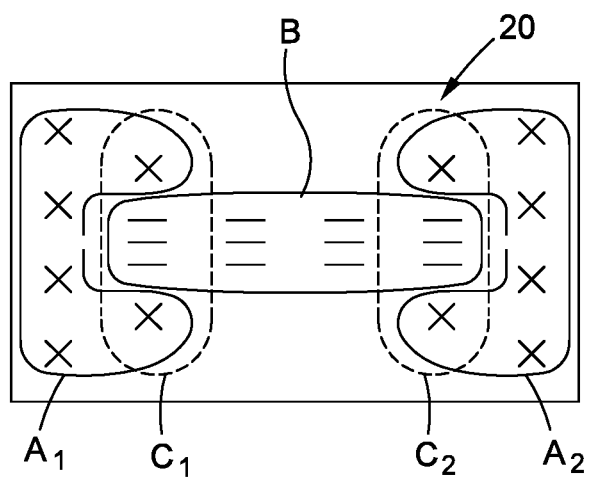

It will thus be appreciated that one or more templates may be utilized to modify a tissue graft in different areas in different ways. As illustrated in FIG. 3F, the tissue graft 20 might be modified in a first area A in a first manner and a second area B in a second manner, thus creating a modified tissue graft which is modified in different ways in different areas. Such modification may result in the modified tissue graft having different characteristics in the different areas. The different characteristics and areas may correspond to different goals, features or characteristics of an anatomical area, including features relating to the anatomy itself and/or a medicant condition which is being treated.

As indicated above, one or more templates might modify the different areas of the tissue graft in different ways (remove areas of material, through-holes, etc.) to create a modified tissue graft having areas of different desired characteristics (adhesion, glide, traction, stress reduction, etc.). Of course, a single tissue graft might be modified in the same or different way in a plurality of areas such as illustrated in FIG. 1F relative to similar areas A1 and A2 (e.g. two areas modified to enhance traction, three areas to increase expansion, etc.). Further, in some cases the different areas (and thus surface modifications) may overlap or transition, such as illustrated relative to areas C1 and C2 in FIG. 3F. Also, as indicated above in FIGS. 3A and 3B, the opposing sides of the tissue graft may be modified or altered in the same or entirely different ways (or only one side might be modified and not the other), depending upon the application.

Figure 4:
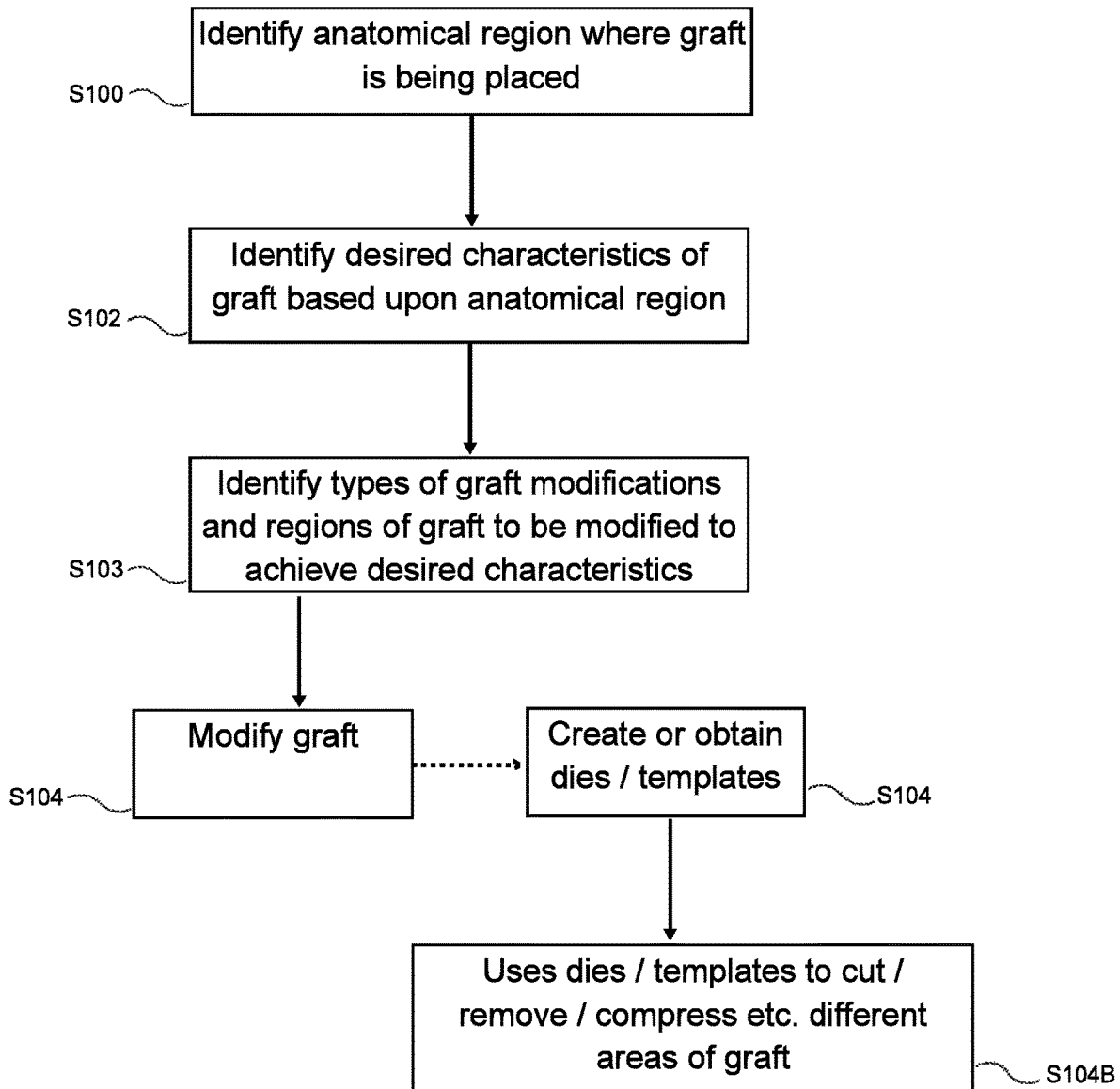
FIG. 4 is a flow diagram illustrating a process in accordance with the invention.

FIG. 4 is a flow diagram illustrating one embodiment of the invention comprising a process for creating a modified tissue graft. In one embodiment, in a step S100, an anatomical region where a graft is to be placed is identified. This may comprise, for example, anatomical region where a wound, injury or the like exists. Of course, such a region may be identified in various manners, such as by examination, machine scans, etc.

In a step S102, desired characteristics for the graft are identified, such as based upon the anatomical region, characteristics of the injury or wound or the like. Such characteristics might comprise, but are not limited to stress reduction, glide, adhesion, traction, scar reduction, osseous healing and/or integration, disease control, increased rate of healing, etc.

In a step S103, one or more types of graft modifications are identified, along with regions of the graft to be modified, to achieve the desired characteristics. As indicated herein, the graft modifications might comprise one or more of forming cuts, pockets, folds, voids, slots, slits, or other modifications or changes to the graft. Further, the regions might comprise the front and/or back of the graft, or any portions thereof.

In a step S104, the graft is modified to create a modified graft. This step might comprise a step S104A in which one or more dies or templates are obtained or created, such as described herein, which may be used to create the desired graft modifications. Then in a step S104B, the one or more dies or templates may be used to modify the graft, such as by cutting the graft, removing material from the graft, compressing areas of the graft, etc., as described herein.

FIG. 5 illustrates examples of the invention, such as based upon the process just described. As illustrated, in an Example A, a patient may have an injury to a knee or shoulder which requires one or more grafts. The identified anatomical condition may thus comprise the knee or shoulder. The desired characteristic for the modified graft may be that it stabilizes motion, by adhering at either or both ends of insertion and gliding in the middle. It may thus be desired to leave the middle of the graft smooth (for gliding purposes) but to modify the ends of the graft so that they have adhesion characteristics, such as by heavily resurfacing the ends thereof. One or more dies may then be used to resurface the ends of the graft to create a modified graft as illustrated, such as where the one or more dies are used to create cuts or slits in multiple directions, such as illustrated in FIG. 2B.

As illustrated by the other examples in FIG. 5, in order to achieve desired characteristics, different areas of a graft may be modified in different manners, including by the level of modification. For example, as illustrated in Example D, a graft might be modified across its entire surface, but the level of modification might vary in different areas, such as by having ends of the graft heavily modified (such as by a high frequency of interval and/or linear cuts) and by having a middle section less heavily modified (such as by low frequency of interval and/or linear cuts).

Further, as indicated in Example C, the front and back of a graft might be modified in different manners to achieve different characteristics on each side of the graft.

Current medical devices are not applicable for creating the multitude of desired modifications to grafts for each use (such as varying depending upon anatomical site, medical condition, etc.). In accordance with the invention, an apparatus can be used to create the modifications applicable to a specific placement, whether pre- or intra-operatively. In some embodiments, a modified tissue graft may be pre-constructed and then delivered to a hospital or doctor for use (thus eliminating the need for construction of the modified tissue graft at the time of the surgery), while in other embodiments, a modified tissue graft might be designed/created intra-operatively.

For example, measuring, such as through image capture and software analysis, the physical properties of the anatomical site and/or the reconstructive tissue graft and its pre- and post-operative appearance may be utilized to correlate the physical properties of a created modified graft to the site. In this regard, one embodiment of the invention comprises a method of creating templates or other devices to modify a tissue graft, such as to create a multitude of patterns in tissue grafts. Such may consist of pre- or intra-operatively made templates.

In one embodiment, the templates may be based on an analysis of a particular anatomical region, such as software analysis of an image of initial tissue defect, the template designed to allow for a desired graft pattern to reduce the potential pressure, reduce stress, decrease wear and tear, provide traction, or achieve other objectives when implanted or placed at a particular anatomical site. Based on factors such as, but not limited to, the size, shape, thickness, width, variegations, type, and the desired surgical outcome, a tissue graft may be modified to include a pattern or other features. Due to the variability in a defect being reconstructed, such as the abdominal wall, breast, face, and extremities, different template patterns may be generated. Software analysis may be used to create an appropriate tissue graft for an identified existing defect.

In one embodiment, different materials may be used to make the templates and their respective patterns. In a preferred embodiment of the invention, modified grafts may be created which not only permit mesh expansion, but provide for a multitude of various designs, shapes, patterns, variegations and materials to accommodate the existing defect to achieve the desired reconstructive and aesthetic results.

In one embodiment, software and/or hardware may be used to perform a pre-manufacture or pre-operative analysis. Templates may be constructed from a pre-made mold, and be made of different materials such as metal or plastic to be integrated with a compression device. The template can be integrated with a stationary or portable compression apparatus that can create prepackaged tissue grafts in a pre-manufactured configuration by a manufacturer or to be subsequently sterilized and used by a surgeon in the operating room. A primary objective of the invention allows for a tissue graft to be modified to create a tissue graft which is patterned to address or accommodate anticipated problems due to any and all activity and reconstructive and aesthetic results.

In one embodiment, an apparatus, either via cutting, compression and/or removal of segments of tissue (such as by pressing a template, such as a die, into contact with and/or into the surface of the tissue graft), creates a modified tissue graft for reconstruction by creating a desired pattern within a graft. Compression can be used against the template that in turn creates the desired pattern.

While in certain embodiments templates, including dies, punches and the like may be used to modify a tissue graft, other apparatus may be used. For example, lasers, water knives or the like may be used to modify the tissue grafts.

The templates or other apparatus which are used to modify a tissue graft to create a modified tissue graft may be made of a variety of materials, including synthetics, plastic, and metals; the templates or other apparatus may be used in a manufacturing facility or operating room; the templates or other apparatus may be operable by manual pressure, air pressure, hydraulic pressure, or electrically driven apparatus such as motor driven presses or screws, including via a portable compression device. As one example, pneumatic press may be used to apply pressure on the template or die to press it into engagement with the graft.

One embodiment of a template or die is illustrated in FIGS. 7A-D. As illustrated, this template may comprise a cutting die 700. In the embodiment illustrated, the cutting die 700 has a base 702 with a top surface having a cutting grid 704 extending therefrom. The cutting grid 704 may define a grid of cutting surfaces or blades 706. Preferably, as illustrated, the cutting surfaces or blades 706 may comprise rows and columns of cutting blades that insect, thus forming a grid of generally quadrilateral (such as rectangular, but potentially square) cutting elements.

In one embodiment, the base 702 may be constructed of a polymeric material, although other materials might be used. For example, the base 702 might comprise a generally solid piece of DuPont Delrin®. The cutting grid 704 may be constructed from 301 stainless steel.

In one embodiment, as illustrated, the cutting die 700 has the following dimensions: A—12.70 mm; B—11.11 mm; C—20.00 mm; D—10.00 mm; E—80.00 mm; F—185.40 mm; and θ—42 degrees. Of course, the cutting die 700 might have other shapes and sizes, including having a cutting grid 704 which has a different shape (it could be a grid of squares, triangles, circles or even irregular shapes). It will be appreciated that the depth of cut of the die 700 is dependent upon the distance that the blades 706 extend outwardly from the base 702. As detailed below, the cutting depth might be variable, such as by changing the distance the blades 706 extend outwardly, by using one or more intermediate stops (between the base 702 and ends of the blades 706).

In use, the cutting die 700 may be oriented so that the cutting grid 704 is placed against a tissue graft. A force may then be applied to the cutting die 700 to press the blades 706 into the tissue graft. In one embodiment, the cutting die 700 may be pressed into the tissue graft until the base 702 is against the tissue graft (a full depth cut). In other embodiments, the blades 706 may be pressed into the tissue a lesser distance, such as depending upon the desired depth of cut. The cutting die 700 may then be removed from the tissue graft. This process results in the surface of the tissue graft being modified to include a "grid cut" which matches the configuration of the cutting grid 704. In one embodiment, this grid cut causes the tissue graft to have modified or altered characteristics.

Another embodiment of a template or die is illustrated in FIGS. 8A-8E. As illustrated, this template may comprise a cutting die 800. In the embodiment illustrated, the cutting die 800 has a base 802 with a top surface having a cutting grid 704 extending therefrom. The cutting grid 804 comprises a plurality of cutting surfaces or blades 806. Preferably, the blades 806 are arranged into a plurality of rows and columns. As illustrated, the blades 806 in each row are be spaced from one another and the blades in adjacent rows are offset from one another in alternating positions.

Figure 8A:
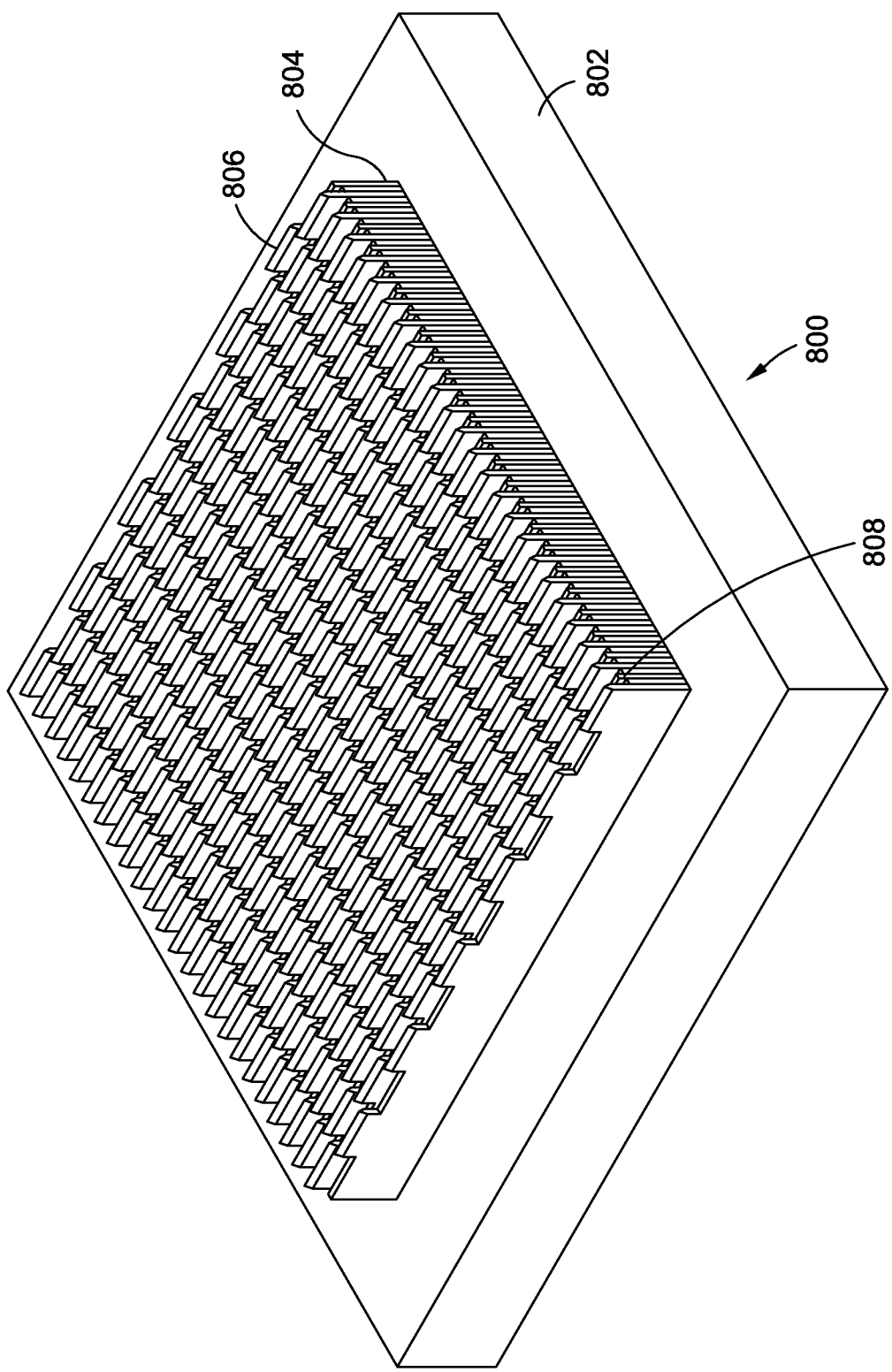
Figure 8D:
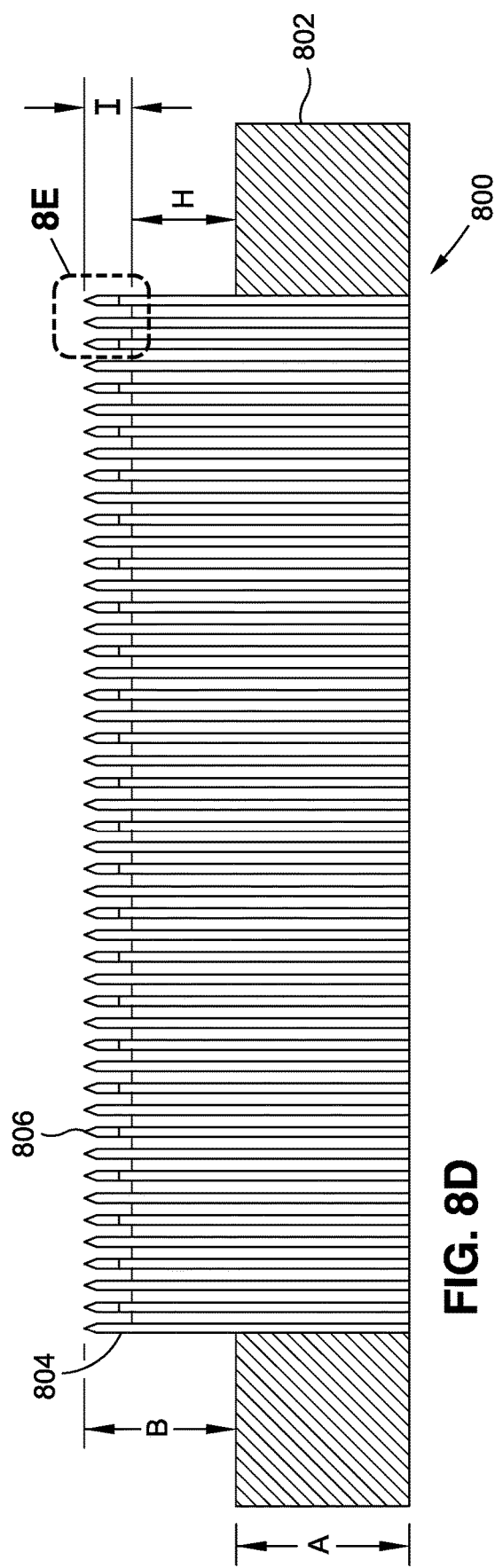
Figure 8E:
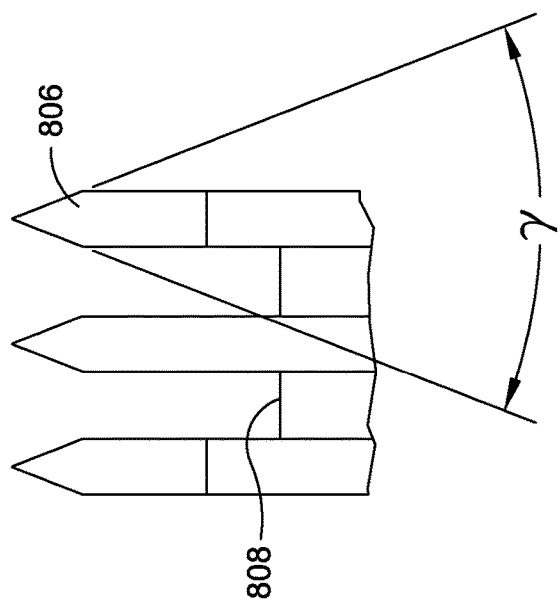

As best illustrated in FIG. 8E, but visible in FIGS. 8A and 8D, in one embodiment, spacers 808 may be located between the blades 806. These spacers 808 may be used to control the depth of cut or penetration of the blades 806 by serving as a stop. In one embodiment, the spacers 808 might be removable or interchangeable, such as whereby spacers of different heights may be inserted between the blades 806 to change the depth of cut or penetration. In one embodiment, the number of spacers 808 might vary, such as by not having spacers in the spaces between all of the blades. In another embodiment, the depth of cut might be controlled simply via the height of the blades 806 from the base 802, or in a configuration in which the distance that the blades 806 extends out of the base 802 may vary (such as where the blades can be moved relative to the base, thus allowing the blades to extend through the base 802 by varying distances).

Once again, the base 802 may be constructed of a polymeric material, although other materials might be used. For example, the base 802 might comprise a generally solid piece of DuPont Delrin®. The cutting grid 804 may be constructed from 301 stainless steel.

The cutting die 800 may again have a variety of shapes and sizes. In one embodiment, as illustrated, the cutting die 800 has the following dimensions: A—12.70 mm; B—11.11 mm; C—6.35 mm; D—6.35 mm; E—1.6 mm; F—75.92 mm; G—76.20 mm; —7.62 mm; I—3.49 mm; γ—42 degrees.

Use of the cutting die 800 may be similar to that illustrated described above, wherein the cutting die 800 may be placed into engagement with a tissue graft and the blades 806 may be pressed into the tissue graft. Use of this cutting die 800 may create a pattern of cuts similar to that illustrated in FIG. 2A and described above. Such a pattern of cuts may create a tissue graft which has modified characteristics whereby the graft is expandable.

As described above, one aspect of the invention is a specially configured template or die having one or more blades or other cutting elements, and one or more secondary surfaces, such as stops. For example, the template or die may comprise one or more central blades and lateral or exterior surfaces, such as flat or non-flat recessed surfaces at one or more elevations (relative to the blades), such as for use in controlling or defining a depth of cut of the blades. The stop surfaces might be located between one or more blades, and/or be located at or around an area containing the blades.

In some embodiments, multiple templates or dies may be utilized, including by combining different templates or dies together to form a single template or die which is then capable of modifying a graft in different manners in different locations.

In one embodiment, the orientation of a template or die may be used to create different surface patterns or other graft modifications. For example, a template or die having a number of parallel blades might be pressed into engagement with a graft at a first orientation, and then rotated to one or more other orientations and then re-engaged with the graft (such as at 0 degrees, 90, 180, 270 and/or 360 degrees, or other angles or orientations), whereby the blades create cuts (such as partial thickness cuts) at a plurality of different angles or orientations.

As indicated herein, the reconstructive graft may include various surface or other features, including for enhancing the retention of medicants or other materials (unless otherwise indicated, the term "medicants" as used herein may include medicants, tissues or other materials, as described below). In one embodiment, for example, surface features such as projections, channels, depressions, voids, pockets or the like may be formed in or through the tissue graft for accepting one or more medicants (including but not limited to chemotherapeutics, antibiotics, growth factors or other drugs), other tissues (including human non-human tissue, synthetic tissue, stems cells or the like) or other materials such as rebar (or other supportive or strengthening materials). In one embodiment, the modified tissue graft may be pre-created with such features and then the medicants, other tissues or materials may be associated with the reconstructive tissue graft at a later time, such as before or during surgery. In other embodiments, a modified tissue graft may have such materials pre-associated. For example, a tissue graft may be modified by forming one or more pockets, sleeves, folds, voids or the like, and one or more medicants, tissues or other materials may be associated with those pockets or voids during manufacture. The pre-configured, pre-medicated reconstructive tissue graft may then be provided to the surgeon for use. It will be appreciated that while medicants may be associated with a modified tissue graft, other materials might also be associated, such as other types of tissue (as described above), bone material, or even metal meshes, or a variety of other materials (such as depending upon the particular anatomical region and/or condition for which the modified tissue graft is intended).

The templates of the invention and/or other apparatus may be used to place such medicants or other materials. For example, one template may be used to modify the tissue graft, such as by creating the surface patterns, while other apparatus or devices may be used to associate the medicants or other materials (such as a medicant implanter, etc.). In other embodiments, these functions may be combined (such as by having the template modify the graft and place the medicants or other materials or facilitate their placement by associated apparatus).

Figure 6A:
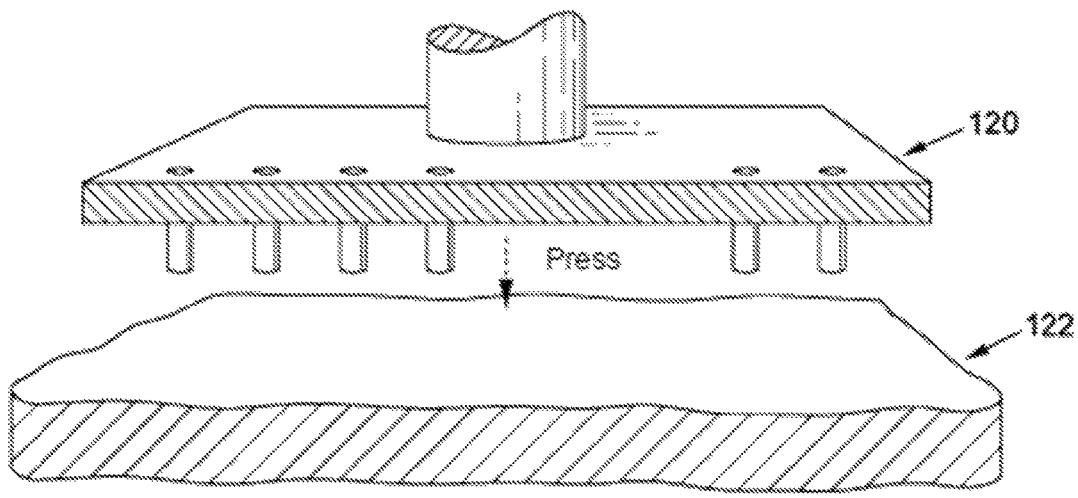
FIGS. 6A, 6B, and 6C illustrate a method of modifying a tissue graft with a template to create a modified tissue graft having one or more surface patterns and associating one or more medicants with said surface patterns in accordance with an embodiment of the invention.
Figure 6B:
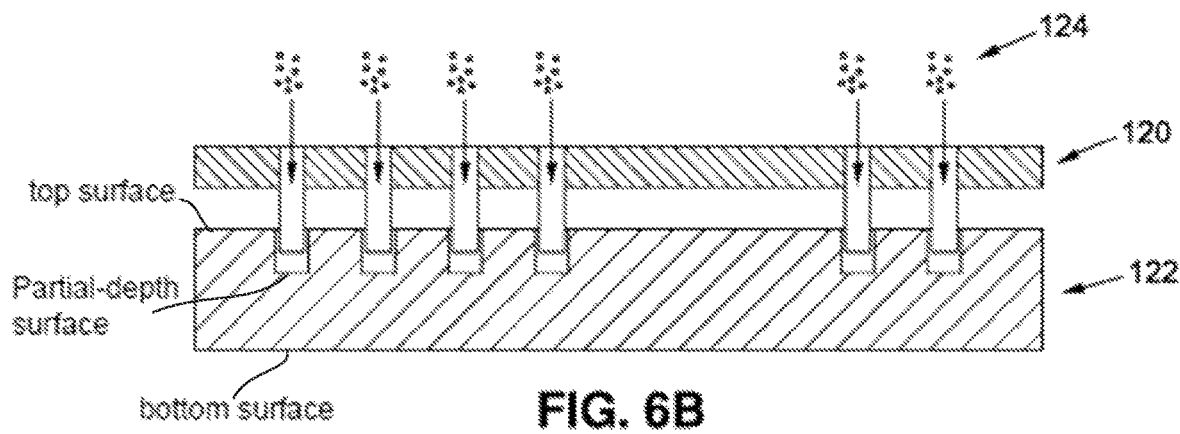
Figure 6C:
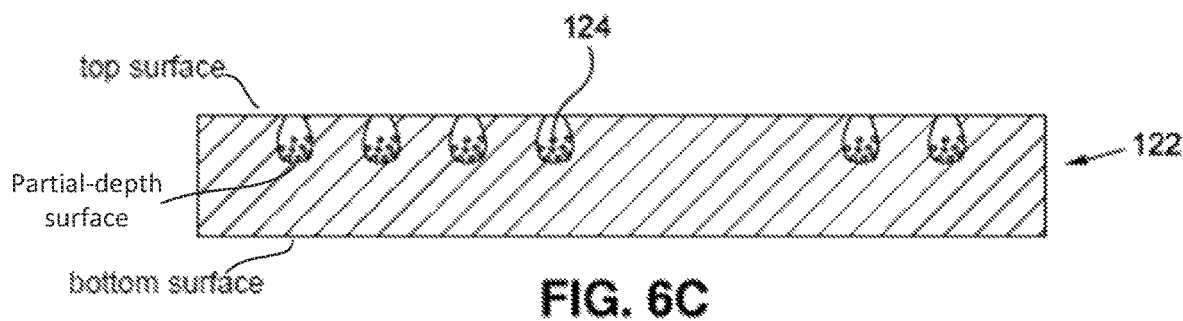

For example, FIG. 6A illustrates use of a template 120 to modify a tissue graft 122, such as by using the template 120 to cut or remove portions of a surface of the graft 122. As illustrated in FIG. 6B, the template 120 or another device may be used to associate a medicant 124 (or other material such as tissue, as described above) with one or more of the created surface features. FIG. 6C illustrates one embodiment of a modified graft 122 which includes one or more surface features and an associated medicant 124. This pre-prepared modified graft 122 may then be located in a particular anatomical area of a patient.

As indicated, the template 120 may have various configurations and constructions. For example, the template 120 might have the form of a punch. In other embodiments, the template 120 might have the form of one or more dies, such as cutting or stamping dies. In some embodiments, more than one template 120 might be used, such as by applying a first template in one or more first areas and a second template in one or more second areas, or applying a first template to a first area and then a second template to the same area.

Figure 6D:
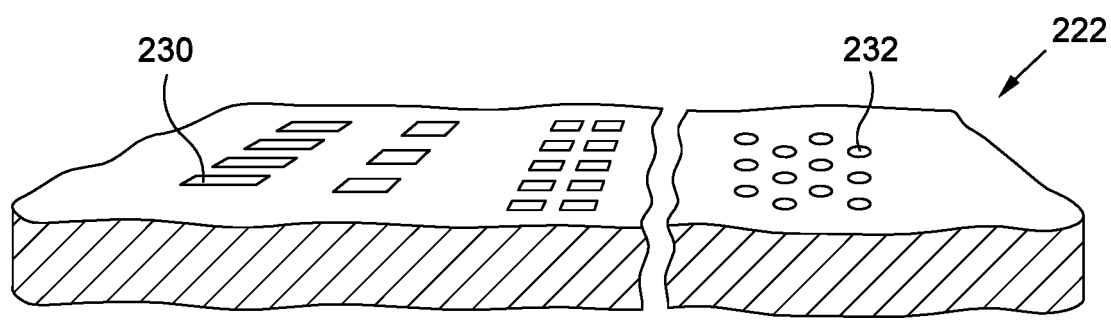
FIGS. 6D and 6E illustrate additional embodiments of a modified tissue graft in accordance with the invention.

FIG. 6D illustrates another embodiment of a modified graft 222 in accordance with the invention. As illustrated, the modified graft 222 may include one or more surface modifications, such as slots 230 which facilitate controlled expansion of the modified graft, such as described above. The modified graft 222 might, in addition or alternatively, include one or more features 232 which retain medicants. In one embodiment, the medicant retaining features are configured to evenly/spatially distribute the associated medicants. As illustrated, this may be accomplished by evenly distributed medicant retaining features. However, as one aspect of the invention, the medicant retaining features may have varying sizes or locations which are configured to cause associated medicants to be distributed in other controlled fashions (such as accounting for factors such as the configuration of the modified tissue graft, including varying thickness thereof, and anatomical features where the graft is to be placed, such as higher or lower blood flow in regions adjacent to the graft when implanted).

Figure 6E:
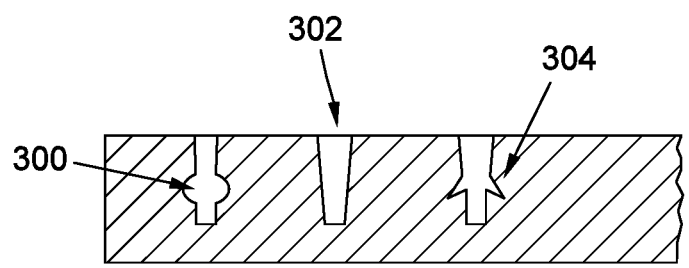
Figure 7D:
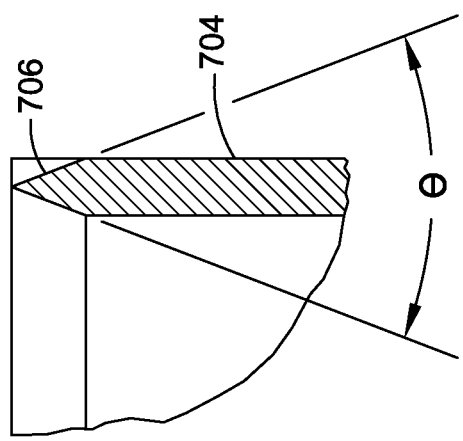
Figure 7A:
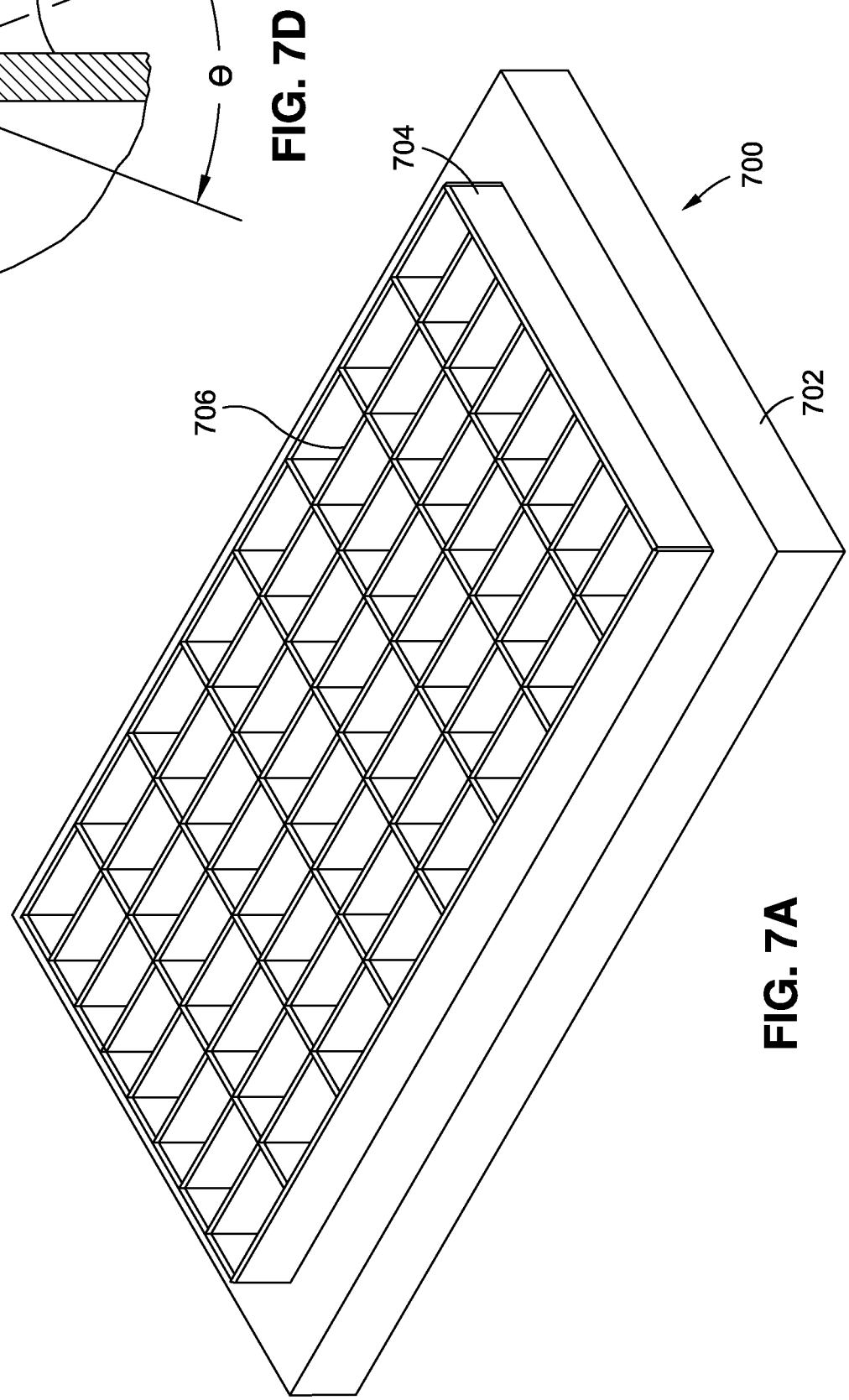

FIG. 6E illustrates different medicant retaining features. As one example, a medicant retaining feature may comprise or include a void, such as a bulbous cavity 300 formed in the tissue graft. As another example, the feature might comprise a void or cavity which includes a valve 302. The valve 302 may be used to retain the medicants in the graft during placement and/or control the flow or release of medicant or other materials from the associated cavity to the exterior of the graft. The valve 302 might, for example, be formed of a portion of the tissue graft itself, such as an upper layer of the tissue graft which is perforated or slit. As yet another example, the feature might comprise a punch-type feature 304 which includes one or more voids, cavities, pockets or the like which can be used to retain medicants. Of course, as indicated herein, the size and shape of the medicant retaining features may vary.

In one embodiment, the medicant retaining feature is intended to retain one or more medicants (or other materials, as described herein) for release once the tissue graft is located at the desired anatomical site. In other embodiments, the retaining feature might retain the medicant or other material once the graft is placed. For example, a synthetic mesh material which is located in the graft may remain in the graft after it is placed, thus strengthening the graft and/or the integration of the graft with the anatomical site.

The medicant retaining feature may be used as part of other aspects of the invention, such as the targeted resurfacing feature described above relative to FIG. 4. Referring to Example F, a center or middle section of a graft might be modified, such as by interval and/or linear modification, to create an adhesion characteristic. This same region may be modified to include one or more pockets, voids or other medicant retaining features with which one or medications (such as cancer treating pellets) might be associated. The ends of the graft may then either not be modified or might be modified in other manners.

Example G in FIG. 4 illustrates another configuration in which a modified graft is configured to be used in an area infection. The graft may be modified to have an adhering characteristic and include medicant retaining features with associated medicant for treating the infection. In this manner, the adhesion characteristic aids in maintaining the graft in position at the treatment site and the medicant is then released and absorbed at the site.

In accordance with another embodiment of the invention, a modified tissue graft may be constructed from or comprise two or more graft layers to comprise a "multi-layer" tissue graft. Further, such a modified tissue graft may preferably have medicants such as those described herein, associated therewith.

Figure 9:
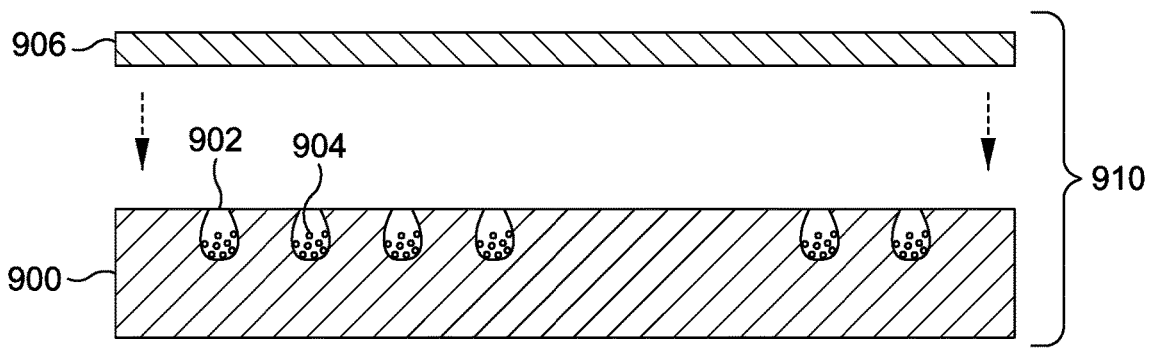
FIG. 9 illustrates aspects of a method of forming a multi-layer modified tissue graft in accordance with the present invention.

Referring to FIG. 9, in one embodiment, a base tissue graft 900 may be created as described above, wherein the graft is modified to include one or more medicant retaining or associating features 902 (and may be modified to include other features or enhancements as detailed above, such as to have specific characteristics for a particular anatomical region or medical condition). One or more medicants 904 may then be associated with the base graft 900, such as illustrated in FIG. 6C. In accordance with the invention, at least one secondary layer of tissue 906, such as an amnion membrane allograft, may be placed thereover, such as illustrated in FIG. 9. This creates a multi-layer modified tissue graft 910. In this manner, the medicants are trapped or retained in the base tissue graft.

Of course, the one or more secondary tissue layers may be associated with one or both sides of the base graft, such as depending upon whether medicants are associated with one or both sides thereof. The secondary tissue layer(s) may be connected to the base tissue graft in various manners, including via adhesive materials, by mechanical engagement (such as by pressing the secondary tissue layer(s) into engagement with the base tissue graft, such as via one or more punches, blades, etc.).

It will also be appreciated that the two tissue grafts or layers may comprise the same and/or different materials, such as different types of tissue. For example, the base modified tissue graft layer might comprise a cadaveric human tissue and the secondary tissue layer might comprise a synthetic tissue layer (including with medicant contained within).

Figure 10A:
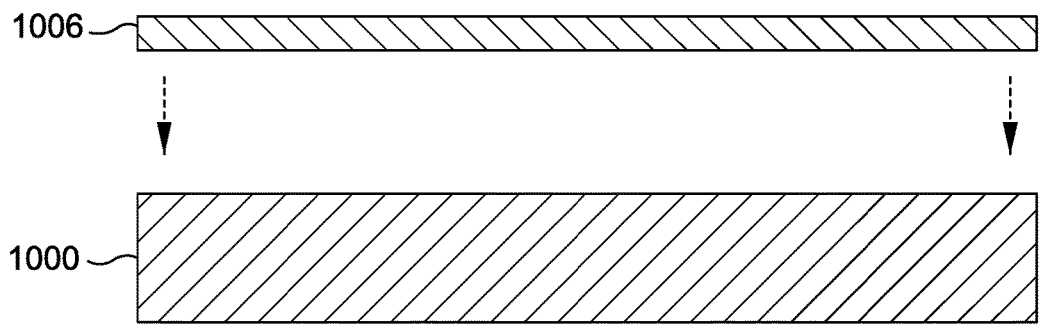
FIGS. 10A and 10B illustrate aspects of a method of forming a multi-layer modified tissue graft in accordance with another embodiment of the invention.
Figure 10B:
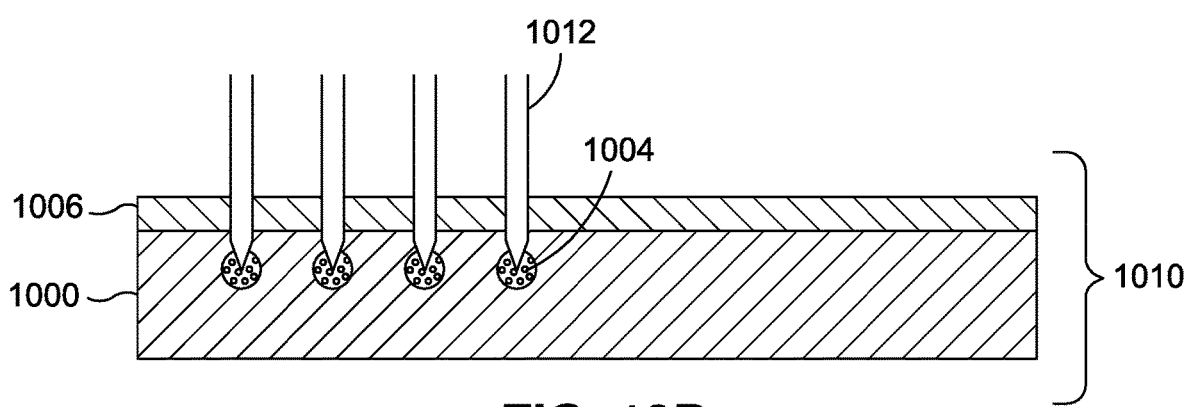

Referring to FIGS. 10A and 10B, in another embodiment, a base tissue graft 1000 may be created as described above, wherein the base graft is modified to include one or more features or enhancements as detailed above (and not shown in FIG. 10A). At least one secondary layer of tissue 1006, such as an amnion membrane allograft or a medicant containing sheet, may be placed onto the base tissue graft (again, at one or both sides), such as illustrated in FIG. 10A. Again, the secondary tissue layer(s) may be connected to the base tissue graft in various manners.

Thereafter, medicants or other materials may be imprinted or injected through the secondary tissue layer(s) 1006 into the underlying base tissue graft 1000 or between the base tissue graft and the secondary tissue layer(s), such as illustrated in FIG. 10B. For example, one or more needles 1012 (or blades or other penetrating elements) may be pressed through the secondary tissue layer(s) 1006 and into the base tissue graft 1000, where the needles either push medicants 1004 through (imprint) the secondary tissue layer(s) or are used as a conduit through which medicants are passed (inject). Of course, other methods and devices might be used to associate medicants with the base tissue layer of such a modified multi-layer tissue graft.

In yet another embodiment, a base tissue graft may be crated as described above, wherein the base graft is modified to include one or more features or enhancements as detailed above. A medicant graft may then be prepared or obtained. Such a medicant graft might comprise, for example, a secondary tissue graft or sheets of prepared medicants having medicants (and which medicants may be have various concentrations or dosages) associated therewith. The secondary tissue graft might comprise, for example, an amnion membrane allograft. Such a graft may then have medicants associated therewith (such as by modifying the graft to include medicant retaining features as described herein and then associating medicants therewith, by applying medicants to the exterior of the secondary tissue layer, etc.) to create the medicant graft. The medicant graft is then associated with the base tissue graft to create a multi-layer, medicated modified tissue graft. As described above, the medicated or medicant graft may be connected to the base tissue graft.

In these embodiments, the secondary tissue layer(s) may also be modified to include features or enhancements like the base tissue graft.

As described herein, the secondary tissue graft might comprise an amnion membrane allograft. However, the secondary tissue graft might comprise other types of grafts, such as a chorion membrane allograft or other types of grafts as described herein, including synthetic graft materials.

It will be appreciated the type and nature of the graft modifications in accordance with the invention may vary and be wide ranging, such as based upon the anatomical area and desired characteristics. Further, the modified tissue grafts may be utilized in a variety of anatomical locations. In one preferred embodiment, the modified tissue grafts are external tissue grafts (e.g. used in an external location). In such a configuration, the external tissue grafts may be particularly configured to facilitate/expedite wound healing with minimal scarring.

The above description represents various embodiments of the present invention. However, many variations to the method and apparatus are possible without deviating from the scope of the invention. It will be understood that the above described arrangements of apparatus and the method described herein are merely illustrative of applications of the principles of this invention and many other embodiments and modifications may be made without departing from the spirit and scope of the invention as defined in the claims.

What is claimed is:

1. A modified tissue graft prepared by the process of:
obtaining a tissue graft having a top surface and a bottom surface;
obtaining a template comprising a plurality of cutting blades and one or more stop surfaces, and
pressing said template downwardly into engagement with at least one of said top surface and said bottom surface of said tissue graft until said one or more stop surfaces engage said tissue graft, whereby said plurality of cutting blades create a plurality of corresponding partial-depth cuts in said tissue graft.

2. The modified tissue graft in accordance with claim 1, wherein said plurality of blades are located in parallel rows, wherein blades in each row are spaced from one another.

3. The modified tissue graft in accordance with claim 2, wherein blades in adjacent rows are offset from one another.

4. The modified tissue graft in accordance with claim 1, wherein said blades are configured into a grid pattern.

5. The modified tissue graft in accordance with claim 1, wherein said one or more stop surfaces comprises a base of said template and said plurality of blades extends outwardly from said base.

6. The modified tissue graft in accordance with claim 1, comprising pressing said template downwardly using a pneumatic press.

7. The modified tissue graft in accordance with claim 1, wherein said tissue graft is configured to comprise human tissue.

\* \* \* \* \*